United States Patent
Osinga et al.

(10) Patent No.: US 9,532,560 B2
(45) Date of Patent: Jan. 3, 2017

(54) MOSQUITO EXTERMINATOR BASED ON INFECTION/CONTAMINATION BY A FLOAT PROVIDED WITH A POWDERED COATING

(71) Applicant: IN2CARE HOLDING B.V., Wageningen (NL)

(72) Inventors: Anne Jurjen Osinga, Rockanje (NL); Marit Farenhorst, Wageningen (NL); Remco Alexander Suer, Wageningen (NL); Bart Geert Jan Knols, Dodewaard (NL)

(73) Assignee: IN2CARE HOLDING B.V., Wageningen (NL)

( * ) Notice: Subject to any disclaimer, the term of this patent is extended or adjusted under 35 U.S.C. 154(b) by 61 days.

(21) Appl. No.: 14/412,545

(22) PCT Filed: Jun. 28, 2013

(86) PCT No.: PCT/NL2013/050467
§ 371 (c)(1),
(2) Date: Jan. 2, 2015

(87) PCT Pub. No.: WO2014/007611
PCT Pub. Date: Jan. 9, 2014

(65) Prior Publication Data
US 2015/0121746 A1    May 7, 2015

(30) Foreign Application Priority Data
Jul. 4, 2012  (NL) ..................................... 1039713

(51) Int. Cl.
*A01M 1/02* (2006.01)
*A01M 1/20* (2006.01)
(Continued)

(52) U.S. Cl.
CPC ............... *A01M 1/02* (2013.01); *A01M 1/106* (2013.01); *A01M 1/2016* (2013.01); *A01N 25/34* (2013.01); *A01N 49/00* (2013.01); *A01N 63/04* (2013.01)

(58) Field of Classification Search
CPC ...... A01M 1/02; A01M 1/106; A01M 1/2016; A01N 25/34; A01N 63/04
See application file for complete search history.

(56) References Cited

U.S. PATENT DOCUMENTS 2,208,997 A * 7/1940 Medler ................. A01M 1/02
239/45
4,638,592 A * 1/1987 Schneidmiller ......... A01M 1/02
426/1

(Continued)

FOREIGN PATENT DOCUMENTS

| GB | 2 419 531 | 5/2006 |
|---|---|---|
| GB | 2 426 196 | 11/2006 |
| WO | 03 051112 | 6/2003 |

OTHER PUBLICATIONS

International Search Report Issued Oct. 7, 2013 in PCT/NL13/050467 Filed Jun. 28, 2013.

*Primary Examiner* — Gary Hoge
(74) *Attorney, Agent, or Firm* — Oblon, McClelland, Maier & Neustadt, L.L.P.

(57) ABSTRACT

An exterminator for insects, for example mosquitoes, including: a) a container open on an upper side and filled with a water-containing fluid, including an inner wall with a smooth surface descending steeply towards the fluid, b) a cover at a distance above the open upper side of the container, and c) a float in the container, under the cover, and which can move up and down with the fluid level. The float includes a float body which extends above the surface of the fluid and which includes a structure which remains dry in a form of a gauze, net, cloth, screen, grid or fabric, on to which (Continued)

an electrostatic coating layer in a form of a platinum complex-containing silicone composition is provided.

14 Claims, 1 Drawing Sheet

(51) Int. Cl.
*A01N 25/34* (2006.01)
*A01M 1/10* (2006.01)
*A01N 49/00* (2006.01)
*A01N 63/04* (2006.01)

(56) References Cited

U.S. PATENT DOCUMENTS

| | | | | |
|---|---|---|---|---|
| 5,896,697 | A * | 4/1999 | Kang | A01M 1/02 43/107 |
| 6,189,259 | B1 * | 2/2001 | Soller | A01M 1/2005 43/131 |
| 2006/0090391 | A1 * | 5/2006 | Huang | A01M 1/106 43/107 |
| 2009/0126257 | A1 * | 5/2009 | Banfield | A01M 1/106 43/121 |
| 2012/0311919 | A1 * | 12/2012 | Hardigree | A01M 1/106 43/107 |

* cited by examiner

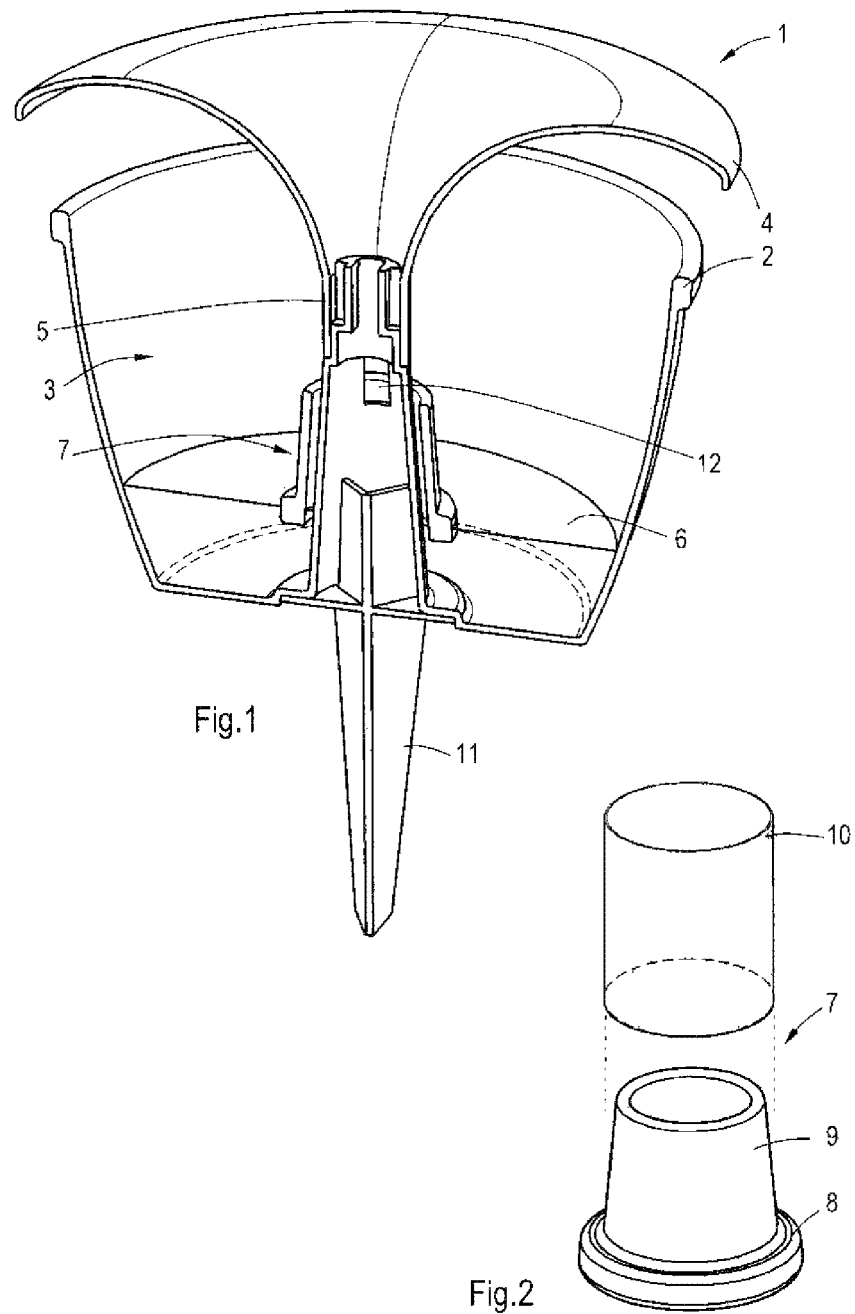

MOSQUITO EXTERMINATOR BASED ON INFECTION/CONTAMINATION BY A FLOAT PROVIDED WITH A POWDERED COATING

The present invention relates to an exterminator for infecting and eventually exterminating insects, in particular mosquitoes.

The present invention further relates to a packaging, in particular a water-soluble packaging which is provided with a structure which is to be provided in the exterminator and which comprises active constituents for getting rid of, in particular, mosquitoes and their larvae.

Mosquito exterminators based on insecticides are generally known. It is also known, however, that their effectiveness is often comparatively short-lived, because insects such as mosquitoes can develop resistance to insecticides.

It is an object of the present invention to provide an improved exterminator which can be used to get rid of at least one or more types of mosquitoes, and which additionally can be active in a durable and effective way and which can be applied in combination with various active constituents.

To achieve this, the exterminator according to the invention comprises the characteristics of claim 1.

The advantages of the exterminator according to the invention are manifold. As the inner wall having a smooth surface descends steeply to the water-containing fluid, mosquitoes will not feel inclined to land on it, owing to the smooth surface of the wall which does not give a good grip. In addition, a cover is provided above the open upper side of the container, at a distance such that flying mosquitoes can enter into said container. Partly by virtue of the water vapour gathering under the cover and/or the possibly provided lure(s) for insects, the insect is attracted towards the water gathered in the shielded, seemingly safe moist space under the cover.

In the container, there is provided a float which floats on the water and hence moves up and down with the water level, which float is attractive for mosquitoes to sit on in order to deposit their eggs in the water. For this purpose, the float has a float body which is situated above the surface of the fluid and under the cover, and which hence remains dry, and which can be contacted by the insects.

The exterminator described hitherto constitutes a pleasant accommodation for insects, in particular mosquitoes of the *Aedes* species (which transmit arbo viruses, including dengue) but also for those of the *Anopheles* species (malaria, filariasis) and *Culex* species (arbo viruses, (diro)filariasis), which can be attracted to said accommodation, if necessary, by one or more lures tempting them, in particular, to sit on the float body in order to deposit their eggs in the water gathered underneath the float.

The so-termed software to be explained hereinafter is formed by the combination of powders active on various fronts, which, in practice, are present on the float, in particular on the float body, as well as in and on the water. Infection and/or contamination of the insects by the software takes place when they sit on the float, ridge and/or float body, usually while they are depositing their eggs.

A problem which is also resolved by the invention is formed by the way in which said powders can be provided on a base, in this case a structure such as a gauze, net, cloth, screen, grid or fabric. Scattering said powders over the structure proved ineffective because the powder did not adhere to the structure, as a result of which the mosquitoes sitting on the structure did not come into contact with the powder(s) when they deposited their eggs in the aqueous fluid, which minimized the effectiveness of the intended extermination to an already known level. Therefore, an electrostatic coating layer in the form of a platinum complex-containing silicone composition was selected, which was first provided on the structure. Surprisingly, it was found that this electrostatic coating layer did adhere to said structure. Subsequently, said one or more powders were applied to said electrostatic coating layer which, surprisingly, were found to adhere well to said coating layer, without hormone and/or fungus, whether or not with an intensifying agent, being attacked thereby or, conversely, said hormone and/or fungus attacking the effectiveness of the coating layer. Finally, it was also found during use, both in the exterminator and on the above-mentioned structure itself, that if a mosquito lands on a structure provided with a coating layer coated with said powder(s), the latter surprisingly became detached from the coating layer and adhered to the legs of the mosquito. As a result, hormone and/or fungus were transported by the mosquitoes themselves to their assembly or breeding places, where the fungus could infect a much larger number of mosquitoes, and the hormone could infect a much larger amount of eggs.

An embodiment of the exterminator according to the invention has the characteristics described in claim 2.

To attract insects, the mosquito exterminator may be provided with one or more lures which can be provided at various locations in and around the exterminator. These lures may be composed of pheromones, which are signalling substances secreted by members of the same species, substances which are released during microbial degradation of organic material, and the like.

Further, detailed, possible embodiments explained in the remaining claims are mentioned together with the associated advantages in the description given hereinbelow.

The exterminator according to the present invention will now be explained in greater detail with reference to the figures mentioned below, in which corresponding elements are indicated by means of the same reference numerals. In the figures:

FIG. 1 is a partial sectional view of a preferred embodiment of the exterminator according to the invention; and FIG. 2 shows the combination of a float and a structure to be provided around it, which is suitable for use in the exterminator of FIG. 1.

FIG. 1 shows an exterminator 1 for, in particular, mosquitoes, comprising a container 2 which is open on the upper side and which comprises a steeply descending inner wall 3 having a smooth surface, such that mosquitoes will not feel inclined to sit on it. The container can be filled with a generally water-containing fluid or with water, on which a film can be provided to reduce evaporation of the water. Mosquito eggs deposited just under the surface of the fluid and requiring oxygen will drown due to the film present on the surface.

A cover 4 is provided above the open upper side of the container 2 and at a distance such that flying insects can enter said container, which cover, in this case, is shown to be cup-shaped with an arched outer surface which tapers off into a subjacent, in this case, hollow shank 5 which opens into the container 2. Water falling on the outer surface may possibly be guided via the hollow shank 5 into container space 6, but it does not remain there as mosquitoes would be able to deposit their eggs in said water. The cover 4 can be adjusted or rotated such that (rain)water cannot enter the container 6, but instead passes through the hollow shank 5 and, via an overflow (not shown), is discharged directly to the exterior, in which case the fluid in the container 2 is not diluted by the incident water. In general, the position of the cover 4 on the hollow shank 5 is adjustable between a first position in which a passage 12 in the shank 5 to the container 2 is open and a second position in which said passage 12 is closed. In said first position, the contents of the container can be readily replenished, either manually or by means of rainwater. Because the shank 5 is provided with an overflow to the exterior, the container will never be filled to a level beyond the water level in question, as any redundant rainwater or redundant manually added water incident on the cover 4 will be discharged to the exterior via the overflow and through the central shank.

The cover 4 can be detached, if required, from the shank 5, so that filling and cleaning of the then easily accessible interior of the container 2 is readily possible.

The exterminator 1 further comprises a float 7, shown in FIG. 2, which can be moved around the shank 5, which may or may not be hollow, and which float is provided in the space 6 of the container 2. Said float 7 is, for example, made of expanded polystyrene or another suitable substance, enabling it to float well on the water in the space 6 and move up and down along the shank 5 with the level of the water. The surface of a ridge 8 of the float 7 which partly projects from the surface of the water and which allows the float to float is provided with a roughness such that insects have a hold on to said surface and at the same time they can deposit their eggs on the surface of the water. The float 7 which can be moved along the shank 5 further comprises an upwardly extending float body 9. The float 7 is provided at a distance around the shank 5 and can be slid from the shank and, if necessary replaced, when the cover has been removed. If the cover 4 is pressed down, it closes the container either partly or completely. If, for example, the cover 4 is at least partly transparent, then some insects are more attracted to this than others which prefer a somewhat darker, or completely dark, space. Accordingly, container 2 and/or cover 4 can be more or less translucent.

The float body 9 of the float 7 is provided with a structure 10 that fits around said float body, or it constructionally comprises said structure. This structure 10 is provided with an electrostatic coating layer or coating to which powders in dry or formulated (=compounded) form are adhered, notably in such a manner that powder transfer to the legs of the insect present on the structure 10 takes place in an effective manner during the time that it deposits its eggs or when it is present on the structure 10 for another reason (for example as a place to rest).

The container 2 shown in FIG. 1 is in the shape of a flower pot with a cover 4 and a hollow shank 5 which extends centrally through said container. By virtue thereof, a comparatively readily manufacturable, rotationally symmetrical mosquito exterminator 1 is obtained. As is further shown, on the lower side of the shank 5, it opens into a space in which a pin 11 can be provided which can optionally be driven into the ground.

To attract insects, the mosquito exterminator 1 can be provided with one or more lures. These can be added in different ways, such as in a carrier (for example a polymer) which provides for a slow release of the active lure(s) over a prolonged period of time, said active lures being provided in the water or on the lower side of the cover 4. It is also possible that the lures are released directly by container 2 by adding them in the production process of the container to the materials used to manufacture the container. These lures preferably comprise pheromones, which are signalling substances secreted by members of the same species, substances which are released during microbial degradation of organic material, and the like.

Once insects have been lured into the space 6, the exterminator 1 is active on various fronts and at the same time against both the insects and their offspring in the exterminator itself as well as the aquatic stages in other breeding places. For this purpose, the float body 9 and/or the detachable, replaceable structure 10 are provided with the electrostatic coating layer with the adherent dry, possibly formulated powders, such as pyriproxyphene, a juvenile hormone, spores of entomopathogenic (insect-killing) fungi, or synthetic or non-synthetic silica or diatomaceous earth, single or in combination(s).

Preferably, the electrostatic coating layer comprises a silicone composition in the form of a crosswise silicone composition, and the amount of platinum comprised therein is approximately 5 ppm with respect to the silicone composition. The powders adhere well to this coating layer. For details of the composition of the coating layer, reference is made to WO-2009048324, which is considered to be incorporated herein by reference.

Pyriproxyphene has been found to be excellently suited to contaminate mosquitoes and subsequently bring about dissemination of this substance to other breeding places. Entomopathogenic fungi, including the spores of *Beauveria bassiana*, and/or *Metarhizium anisopliae* are very active against mosquitoes, in particular those belonging to the *Anopheles, Culex*, and *Aedes* species. Infection with spores of these fungi cause the grown mosquito to succumb after 6-20 days as a result of the release of toxic substances by the fungus in the mosquito after penetration of the cuticula. Synergy with the action of fungi takes place if an intensifying agent in the form of a powder is additionally applied to the electrostatic coating, which powder, upon contacting the insect's cuticula, in particular the fat present thereon, dissolves and causes the cuticula to desiccate. As a result, via the partly affected place of contact, the fungus can more easily penetrate the skin of the insect. Good examples of intensifying agents are synthetic or non-synthetic silica, or diatomaceous earth, which is a fossilized plankton. It has further been found, however, that these intensifying agents by themselves are also effective already in exterminating insects in combination with the mosquito exterminator 1.

When the structure 10 is no longer effective, it can be readily substituted, by removing the cover 4, with a new structure 10 provided with effective powder. Additional software can always be supplied in a simple manner by sending the structure 10 in a (water-soluble, for example polyvinyl acrylate) packaging, which structure is to be extended from the flat state and thus forms a spatial structure which can be placed around the float body 9, after which the cover 4 is provided again. A structure 10 made of polyester and/or natural materials such as textile, cotton and/or paper, or a combination of polyester and cotton, is preferred.

The container 1 can be made of biodegradable synthetic resin or polyethylene or clay, and the cover 4 can be made of glass, synthetic resin or alternative transparent materials.

In developing countries, where in the various accommodations (ventilation) openings are often present between walls and roofs, these openings can be covered with structures 10 of gauze, net, cloth, screen, grid or fabric, on to which the aforementioned electrostatic coating layer provided with said powder(s) adhere. In this manner, mosquitoes sitting on the structure are also infected.

It is alternatively possible to employ the exterminator 1 without a fluid, in which case, in the container 1, the coating layer and powder(s) are present, for example, on the float 7 and/or the float body 9 and/or the structure 10.

It is also possible to employ one or more of the above-mentioned powders in combination with insecticides.

The invention claimed is:

1. An exterminator for insects, or for mosquitoes, comprising:
   a) a container which is open on an upper side and which is optionally filled with a water-containing fluid, the container including an inner wall with a smooth surface descending steeply towards the fluid;
   b) a cover provided at a distance above the open upper side of the container; and
   c) a float provided in the container, under the cover, and which moves up and down with the fluid level, the float including a float body which extends above a surface of the fluid and which comprises a structure which remains dry in a form of a gauze, net, cloth, screen, grid, or fabric, on to which an electrostatic coating layer in a form of a platinum complex-containing silicone composition is provided, to which one or more powders are adhered comprising:
      a juvenile hormone, and/or pyriproxyphene, and/or
      a fungus, and/or *Beauveria bassiana*, and/or *Metarhizium anisopliae*, and/or
      an intensifying agent, and/or synthetic or non-synthetic silica, or diatomaceous earth, which dissolves upon contact with a cuticula of the insect, so that when used in combination with the fungus, the fungus can more easily penetrate the insect.

2. The exterminator according to claim 1, further comprising a lure provided against a lower side of the cover, in the fluid, on the float and/or the float body, or provided in the container itself, or integrated in a material of the container.

3. The exterminator according to claim 1, wherein the structure is a structure which can be detachably provided around the float body.

4. The exterminator according to claim 1, wherein the structure can be extended from a flat state to a spatial structure which fits around the float body.

5. The exterminator according to claim 1, wherein the structure is made of polyester and/or natural materials or a textile, cotton and/or paper, or a combination of polyester and cotton.

6. The exterminator according to claim 1, wherein the silicone composition is a crosswise silicone composition, and an amount of platinum therein is approximately 5 ppm with respect to the silicone composition.

7. The exterminator according to claim 1, wherein a substance forming a film on the fluid is added to the fluid, which film counteracts evaporation of the fluid.

8. The exterminator according to claim 1, wherein the cover includes an arched outer surface that makes the fluid collected flow down in a direction of a hollow shank.

9. The exterminator according to claim 8, wherein a position of the cover on the hollow shank is adjustable between a first position in which a passage in the shank to the container is open and a second position in which the passage is closed.

10. The exterminator according to claim 8, wherein the shank includes an outwardly extending overflow.

11. The exterminator according to claim 8, wherein on a lower side of the shank, the shank opens into a space for a pin which can be driven into the ground.

12. The exterminator according to claim 1, wherein the cover is at least partly translucent.

13. A structure, or a structure which, after it has been extended, is fitted as a spatial structure around the float body of the exterminator according to claim 1, which is in a form of a gauze, net, cloth, screen, grid, or fabric, on to which an electrostatic coating layer in a form of a platinum complex-containing silicone composition is provided, to which one or more powders are adhered comprising:
   a juvenile hormone, and/or pyriproxyphene, and/or
   a fungus, and/or *Beauveria bassiana*, and/or *Metarhizium anisopliae*, and/or
   an intensifying agent, and/or synthetic or non-synthetic silica, or diatomaceous earth, which dissolves upon contact with a cuticula of the insect, so that when used in combination with the fungus, the fungus can more easily penetrate the insect.

14. A packaging comprising a flat structure according to claim 13, which packaging is water-soluble.

* * * * *